(12) United States Patent
Rinne et al.

(10) Patent No.: US 7,202,377 B2
(45) Date of Patent: Apr. 10, 2007

(54) PROCESS FOR PREPARING VINYL ACETATE

(75) Inventors: Bernd Rinne, Frankfurt (DE); Stefan Hess, Gross-Gerau (DE); Johann Stamm, Frankfurt (DE); Berthold Nuber, Frankfurt (DE)

(73) Assignee: Celanese Chemicals Europe GmbH (DE)

( * ) Notice: Subject to any disclaimer, the term of this patent is extended or adjusted under 35 U.S.C. 154(b) by 26 days.

(21) Appl. No.: 11/261,319

(22) Filed: Oct. 28, 2005

(65) Prior Publication Data

US 2006/0094896 A1 May 4, 2006

(30) Foreign Application Priority Data

Nov. 4, 2004 (DE) .................. 10 2004 053 184

(51) Int. Cl.
*C07C 67/05* (2006.01)
*G01N 35/08* (2006.01)

(52) U.S. Cl. .................. 560/245; 436/52
(58) Field of Classification Search ........... 560/245; 436/52

See application file for complete search history.

(56) References Cited

U.S. PATENT DOCUMENTS 6,420,595 B1 * 7/2002 Hallinan et al. ............ 560/245

FOREIGN PATENT DOCUMENTS

DE 23 59 286 6/1975

* cited by examiner

*Primary Examiner*—Thurman K. Page
*Assistant Examiner*—Lalitha Nagubandi
(74) *Attorney, Agent, or Firm*—Charles A. Muserlian

(57) ABSTRACT

The present invention relates to a method of saturating ethylene-containing gases with acetic acid before they are fed into a vinyl acetate reactor, in which the acetic acid recovered in the vinyl acetate process is introduced into a column having a countercurrent stripping section and a rectification section and ethylene-containing gas is supplied via the bottom, wherein the liquid taken off at the bottom of the column is divided into two substreams and one substream is pumped back into the column with maintenance of a minimum pumped circulation required for sufficient saturation with acetic acid.

11 Claims, 1 Drawing Sheet

PROCESS FOR PREPARING VINYL ACETATE

Figure 1:
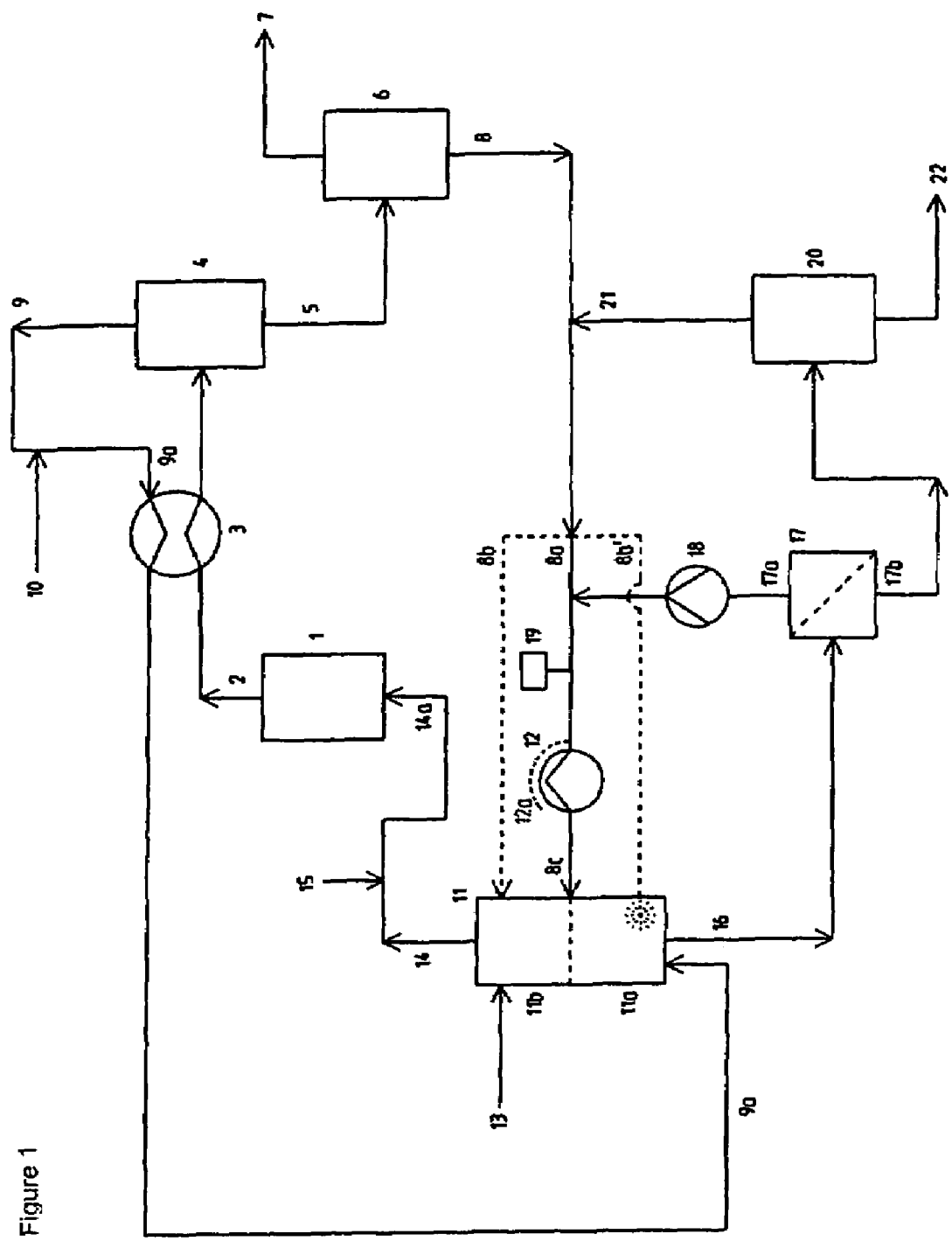

The present invention relates to a process for preparing vinyl acetate in the gas phase from ethylene and acetic acid in the presence of oxygen or oxygen-containing gases, with the reaction mixture fed into the vinyl acetate reactor being saturated with acetic acid.

It is known that acetic acid can be reacted with ethylene and oxygen or oxygen-containing gases in the gas phase at elevated pressure and elevated temperature over palladium-containing fixed-bed catalysts to form vinyl acetate. Supported catalysts comprising palladium together with gold and alkali metal acetates as promoters have been found to be effective catalysts.

Thus, U.S. Pat. No. 4,048,096 discloses a process for producing catalysts comprising palladium, gold and potassium acetate, in which the support material is firstly impregnated with an aqueous solution comprising a mixture of palladium salts and gold salts. Here, the volume of the impregnation solution corresponds to the pore volume of the support material. The impregnation step is followed by a treatment with alkali metal compounds, for example with an aqueous sodium metasilicate solution, as a result of which the metal salts are converted into water-insoluble compounds and immobilized on the support material. Subsequent treatment with a reducing agent reduces the palladium compounds and gold compounds to the corresponding metals. This is followed by impregnation with an aqueous alkali metal acetate solution and a subsequent drying step. A catalyst having a shell structure is obtained.

According to U.S. Pat. No. 5,332,710, the support which has been impregnated with palladium salts and gold salts is dipped into an aqueous fixing solution comprising sodium hydroxide or potassium hydroxide and kept in motion therein for at least half an hour. Here, the support which is completely covered with the fixing solution is rotated from the beginning of the treatment with the fixing solution.

The reaction mixture leaving the vinyl acetate reactor comprises vinyl acetate, unreacted acetic acid and ethylene, small amounts of unreacted oxygen and also inerts, for example carbon dioxide and nitrogen. The reaction mixture is fractionated in a separation vessel downstream of the vinyl acetate reactor to give a gaseous fraction comprising unreacted ethylene and part of the inerts and a liquid product fraction comprising unreacted acetic acid, vinyl acetate and other liquefiable reaction by-products. The gaseous fraction is returned to the process and is also referred to as recycle gas. Vinyl acetate and volatile by-products such as acetaldehyde, methyl acetate and ethyl acetate are separated off from the liquid product fraction by azeotropic distillation with water by known methods, for example as described in U.S. Pat. No. 3,551,299, while acetic acid is obtained in the distillation residue. Vinyl acetate is subsequently freed of methyl acetate and ethyl acetate by methods known per se, for example as described in U.S. Pat. No. 3,458,406. The gas-phase process for preparing vinyl acetate and the work-up of the crude vinyl acetate by distillation are outlined in Ullmann's encyclopedia of industrial chemistry, 5$^{th}$ edition 1996, volume 27, pages 423 to 426.

For the process to be carried out safely, adherence to the ignition limit in the recycle gas is of great importance. The ignition limit depends essentially on the acetic acid content of the recycle gas and the ignition limit in the state saturated with acetic acid is higher than in the state which is free of acetic acid. Sufficient saturation of the recycle gas with acetic acid is therefore of great importance for safe operation of the vinyl acetate process.

Saturation of the recycle gas with acetic acid is carried out using either fresh acetic acid or acetic acid which is recovered in the work-up of the reaction products. For example, acetic acid is recovered from the distillation residue in the distillation to separate off vinyl acetate.

However, the use of the acetic acid recovered from the vinyl acetate process, also referred to as recirculated acetic acid, presents difficulties for the saturation of the recycle gas, since not only acetic acid but also high-boiling compounds and substances of low volatility which tend to polymerize, for example acetoxyvinyl acetate, are present in the recirculated acetic acid. The presence of these impurities leads to fouling in the vaporization apparatus in the saturation process in which recirculated acetic acid is vaporized in the presence of recycle gas and on the heat transfer areas present there, which results in the disadvantage of reduced efficiency of heat transfer in the saturation with acetic acid.

One method of removing high-boiling reaction by-products from the recirculated acetic acid to be circulated before it is fed back into the vinyl acetate reactor is known from DE-A 23 59 286. Here, an ethylene-containing gas, for example recycle gas, is firstly brought into contact with recirculated acetic acid at elevated temperature in an acetic acid vaporizer so as to form a gas stream saturated with acetic acid. This gas stream is subsequently fed via the bottom into a countercurrent stripping column in countercurrent to the recirculated acetic acid to be purified which is introduced at the upper end. In a preferred embodiment, a rectification or absorption section at the top of which fresh acetic acid having comparatively few impurities is introduced is located above the stripping section of the column. The gaseous mixture of acetic acid and ethylene leaving the column contains only small amounts of high-boiling reaction by-products from the recirculated acetic acid, is saturated with acetic acid and can be fed into the vinyl acetate reactor. Fresh ethylene can be added to the process before or after the stripping step.

In the known process, fouling occurs in the acetic acid vaporizer after a prolonged period of operation. The acetic acid vaporizer therefore has to be cleaned at regular intervals and parts of the plant have to be replaced by reserve apparatuses. This cleaning measure results in interruption of the production process.

In addition, passage of the recycle gas saturated with acetic acid through the acetic acid vaporization apparatus results in a pressure drop. As a consequence, a pressure drop upstream of the reactor has to be accepted, and this in turn has an adverse effect on the yield of vinyl acetate, since the vinyl acetate yield depends significantly on the reaction pressure in the reactor.

There is therefore a need for a method which ensures sufficient saturation of the ethylene-containing gas fed into the vinyl acetate reactor using the acetic acid recovered from the vinyl acetate process and does not have the abovementioned disadvantages.

The present invention therefore provides a method of saturating ethylene-containing gases with acetic acid before they are fed into a vinyl acetate reactor, in which the acetic acid recovered in the vinyl acetate process is introduced into a column in which ethylene-containing gas fed in via the bottom is saturated with acetic acid, wherein the column has a countercurrent stripping section and a rectification section and the recovered acetic acid is introduced into the countercurrent stripping section and/or the rectification section and fresh acetic acid is introduced into the rectification section and the liquid taken off from the column is divided into two substreams and one substream is pumped back into the column with maintenance of a minimum pumped circulation required for sufficient saturation with acetic acid, with this substream being monitored in terms of safety and being heated in a heat exchanger arranged in parallel to at least one further heat exchanger before entering the column, and the other substream is discharged.

The minimum pumped circulation which is characteristic of the method of the invention comprises an offtake line for the liquid flowing out of the bottom of the column, a separation apparatus for forming two liquid streams of which one liquid stream is discharged and the other liquid stream is recirculated via a pump and a heat exchanger arranged in parallel to at least one further heat exchanger to the column, which is also referred to as the saturation column. Customary corrosion-resistant stainless steels are used in the minimum pumped circulation.

According to the method of the invention, a minimum pumped circulation of the substream recirculated to the column has to be ensured in order to achieve sufficient saturation of the ethylene-containing gas fed in with acetic acid. For safety reasons, reliable saturation of the ethylene-containing gas fed in with acetic acid is of great importance for subsequent introduction into the vinyl acetate reactor, since the ignition limit of this gas mixture to be fed into the vinyl acetate reactor depends on its acetic acid content and increases with increasing acetic acid content. To ensure reliable saturation of the ethylene-containing gas fed into the saturation column with acetic acid, a sufficient minimum pumped circulation is required and is monitored in terms of safety.

The monitoring in terms of safety is carried out by means of at least two measurement devices for determining throughputs which are each based on a different instrument technology. The monitoring in terms of safety is thus characterized by a quantitative parameter, i.e. the number of measurement devices, and also a qualitative parameter, i.e. the principles of the measurement methods employed. The measurement principles for determining throughputs are known per se to those skilled in the art, for example orifice plate measurement, mass throughput measurement, turbulent throughput measurement, ultrasonic measurement or magnetic-inductive throughput measurement (MID). Since the monitoring of the throughputs in the minimum pumped circulation is based on at least two measurement devices each having different measurement principles, safe operation of the vinyl acetate process is ensured even if one measurement device fails. For example, if one measurement device for determining the throughputs operates according to the ultrasonic method, the other measurement device operates according to the turbulent throughput method.

The minimum pumped circulation required can be derived from the respective operating configuration and is generally at least three times, preferably seven times, the amount of recovered acetic acid introduced into the saturation column.

A heat exchanger is installed in the minimum pumped circulation to heat the liquid to a temperature which ensures that sufficient energy for vaporization of the acetic acid is provided in the saturation column before it enters the saturation column.

To ensure sufficient heat transfer for vaporization of the acetic acid in the saturation column, it is therefore necessary to employ a quite high minimum pumped circulation.

At least one further heat exchanger is installed in parallel to the heat exchanger installed in the minimum pumped circulation. The heat exchangers are operated simultaneously or preferably alternately and can be taken out of the saturation process separately from one another for cleaning purposes without resulting in an interruption to the overall vinyl acetate production process.

The method of the invention dispenses with the known upstream acetic acid vaporizer and fouling problems in the acetic acid vaporizer can be circumvented and the interruption to production necessary for dealing with them can be avoided. As a result of the separately replaceable heat exchangers installed in parallel in the minimum pumped circulation according to the invention, the saturation process in the saturation column can be operated continuously.

The pressure drop occurring at the acetic acid vaporizer likewise no longer occurs, so that a higher pressure can be maintained in the vinyl acetate reactor, which in turn has an advantageous effect on the selectivity of vinyl acetate formation and thus on the capacity of the vinyl acetate plant.

The ethylene to be introduced into the saturation column via the bottom can be pure or be diluted with other gases, for example with nitrogen. However, preference is given to feeding in the ethylene-containing gas stream which is obtained from the reaction mixture leaving the vinyl acetate reactor and is recirculated to the vinyl acetate reactor. In general, this recovered ethylene-containing gas stream is referred to as recycle gas. The recycle gas comprises not only ethylene but also inerts, for example nitrogen or carbon dioxide and also small amounts of oxygen. Fresh ethylene is usually added to this recycle gas before it enters the saturation column.

The saturation column comprises a countercurrent stripping section and a rectification section.

In a preferred embodiment of the method of the invention, the minimum pumped circulation is admixed with the recovered acetic acid. The mixture is subsequently heated in the heat exchanger or exchangers and is introduced into the column at the top of the countercurrent stripping section in countercurrent to the ethylene-containing gas mixture fed in at the bottom of the column, with loading of the gas stream with acetic acid occurring.

However, it is also possible to introduce the recovered acetic acid into the saturation column at a point separate from the point at which the minimum pumped circulation is introduced, either in the countercurrent stripping section or in the rectification section. If the recovered acetic acid is introduced in the countercurrent stripping section of the saturation column, it is advisable to spray the recovered acetic acid into the column.

The recovered acetic acid generally comprises about 5% by weight of water and up to 1% by weight of high boilers, for example ethylene diacetate. The balance to 100% by weight is acetic acid.

A rectification section is arranged above the countercurrent stripping section in the saturation column and relatively pure acetic acid is fed in at the top of this and flows in countercurrent to the ethylene-containing gas which has been saturated with acetic acid. As a result of this measure, further high-boiling impurities which may be present in the recovered acetic acid are removed from the gas stream. This prevents these high-boiling impurities from being carried through to the catalyst-filled vinyl acetate reactor.

The saturation column is generally configured as a tray column. The individual trays are designed in a manner known per se for good contact between liquid and vapor. If appropriate, it is also possible to use a packed column or a series of simple vessels provided at the bottom with gas distributors, for example bubble caps, for the saturation process.

At least one stripping tray, preferably at least two stripping trays, should be installed in the countercurrent stripping section of the saturation column. Furthermore, particularly good results are obtained when at least about five, preferably at least eight, rectification trays are located in the rectification section above the stripping trays. This enables high boilers present in the vapors flowing out from the upper end of the countercurrent stripping section to be returned under reflux to the saturation column.

It is particularly advantageous for the rectification section of the saturation column to be constructed so that the smallest possible amount of liquid is entrained, in order to avoid discharge of high boilers with the gaseous mixture of ethylene and acetic acid which leaves the saturation column via the top of the rectification section as far as possible. For example, it is advantageous to use sieve trays which are constructed and arranged so that very little liquid is entrained in the rectification section.

The liquid flowing out at the bottom of the saturation column is divided in a separation device into two substreams of which one substream is recirculated to the minimum pumped circulation while the other substream is discharged from the saturation process. In general, the weight ratio of the discharged substream to the substream which is recirculated to the minimum pumped circulation is 1:10–20, preferably 1:13–16. The substream which is discharged can be passed to a high-temperature thin film evaporator in which acetic acid is recovered as volatile constituent and is combined with acetic acid recovered at another point of the vinyl acetate process. The high boilers and polymers obtained in the high-temperature thin film evaporator are discharged from the process.

Temperature and pressure in the saturation column can be varied within wide limits, but the pressure is usually maintained at approximately the same level as in the vinyl acetate reactor plus a sufficient pressure difference which is necessary to drive the gas mixture through the saturation column and through the parts of the plant located upstream of the vinyl acetate reactor.

Since the separate acetic acid vaporizer is dispensed with in the saturation method according to the invention, a lower pressure drop than in the prior art is observed in the saturation apparatus for the recycle gas fed in, so that less energy is required for maintaining the sufficient pressure difference.

Likewise, sufficient heat energy for heating the acetic acid present in the minimum pumped circulation for sufficient vaporization of acetic acid in the saturation column to occur is introduced via the heat exchangers arranged in parallel in the minimum pumped circulation. In this way, the ethylene-containing gas fed into the saturation column is saturated with acetic acid at the desired temperatures and at least part of the fresh acetic acid fed in via the rectification section vaporizes into the gas stream conveyed through the countercurrent stripping section.

The composition of the liquid in the minimum pumped circulation corresponds essentially to the composition of the recovered acetic acid with slightly increased proportions of high boilers. An excessively high content of high boilers in the minimum pumped circulation is to be avoided in order to reduce the risk of excessive fouling of the heat exchange surfaces on the heat exchangers in the minimum pumped circulation.

In one advantageous way of operating the saturation column, acetic acid in the form of fresh acetic acid, recovered acetic acid and minimum pumped circulation is fed in in an amount per unit weight of the ethylene-containing gases introduced via the bottom such that the ethylene-containing gas mixture discharged from the saturation column has an acetic acid content of from 10 to 30% by weight at its saturation point.

The amount of recovered acetic acid supplied to the saturation process according to the invention is kept approximately constant and fresh acetic acid is introduced in the rectification section of the saturation column in at least such an amount that a sufficient scrubbing effect is achieved. However, it must also be ensured that the amount of liquid discharged from the saturation process via the separation apparatus is compensated for so that a constant amount of liquid is always present in the minimum pumped circulation and in the saturation column and that the acetic acid discharged from the top of the saturation column in the vinyl acetate reactor is always replaced.

The ethylene-containing gas leaving the top of the saturation column after having been saturated with acetic acid is admixed with the amount of oxygen required for loading the plant fully within the operating parameters before it enters the vinyl acetate reactor.

The accompanying drawing shows, by way of example, a schematic embodiment of the method of the invention.

According to the method outlined in FIG. 1, the gas stream leaving the vinyl acetate reactor 1 via line 2 is firstly cooled in a countercurrent heat exchanger 3 and separated in a separation vessel 4 into a liquid phase and a gaseous phase. The liquid phase comprising crude vinyl acetate is fed via line 5 into a distillation column 6 from which vinyl acetate is taken off at the top via line 7 and is then worked up by further known purification methods which are not shown in FIG. 1. From the bottom of the distillation column 6, recovered acetic acid containing high-boiling impurities is fed via line 8 to the saturation column 11.

The gas stream taken off at the top of the separation vessel 4 is taken off via line 9, admixed with fresh ethylene introduced via line 10 and heated in the countercurrent heat exchanger 3 in which the gas mixture leaving the vinyl acetate reactor 1 heats this gas stream to be recirculated via line 9a. The ethylene-containing gas stream to be recirculated via line 9a is introduced into the saturation column 11 via the bottom. Recovered acetic acid supplied via line 8 is combined via line 8a with the minimum pumped circulation supplied via line 17a, heated in a heat exchanger 12 and conveyed via line 8c to the top of the countercurrent stripping section 11a of the saturation column 11 in which the recovered acetic acid flows in countercurrent to the ascending ethylene-containing gas stream and vaporizes.

In a further embodiment of the method of the invention, all or part of the recovered acetic acid from line 8 can be fed via lines 8b and/or 8b' (shown as broken lines) into the saturation column at a feed point separate from the minimum pumped circulation. In this embodiment of the method of the invention, the recovered acetic acid is usually fed into the rectification section. When the recovered acetic acid is fed into the countercurrent stripping section 11a, it is advisable to spray the recovered acetic acid into the countercurrent stripping section 11a.

The countercurrent stripping section 11a is adjoined by the rectification section 11b at the top of which fresh acetic acid is introduced via line 13 and in which further high-boiling impurities are scrubbed from the ascending ethylene-containing gas stream which is saturated with acetic acid.

The gas which is saturated with acetic acid and is discharged via line 14 is admixed with oxygen, which is supplied via line 15, and then fed via line 14a into the vinyl acetate reactor.

The liquid taken off at the bottom of the saturation column 11 is conveyed via line 16 to a separation apparatus 17 in which a liquid substream is separated off and pumped by means of the pump 18 via the line 17a to the line 8a. In the line 8c, the streams from lines 17a and 8a are combined, heated in the heat exchanger 12 and subsequently introduced into the saturation column 11 at the top of the countercurrent stripping section 11a.

If, in another embodiment of the invention, the recovered acetic acid is fed to the saturation column 11 exclusively via the lines 8b and/or 8b', only the minimum pumped circulation supplied via line 17a is fed into the saturation column via line 8c after passing through the heat exchanger 12.

To monitor the minimum pumped circulation in terms of safety, at least two devices 19 for measuring throughputs, which are each based on different instrumentation techniques, are installed in the minimum pumped circulation.

The other liquid substream obtained in the separation apparatus 17 is discharged via line 17b and, for example, fed to a thin film evaporator 20 in which the stream 21 taken off at the top, which comprises acetic acid, is combined with the recovered acetic acid supplied via line 8, while the high-boiling residue is discharged from the process via line 22.

In addition, at least one further parallel heat exchanger 12a (shown as a broken line) is installed in the minimum pumped circulation. The heat exchangers are preferably operated alternately and can be removed separately for cleaning purposes without the saturation process being interrupted.

For safe operation of the vinyl acetate reaction, sufficient saturation of the reaction gas with acetic acid has to be ensured. This is achieved by maintaining a minimum pumped circulation which is monitored in terms of safety.

What we claim is:

1. A method of saturating ethylene-containing gases with acetic acid before they are fed into a vinyl acetate reactor, in which the acetic acid recovered in the vinyl acetate process is introduced into a column in which ethylene-containing gas fed in via the bottom is saturated with acetic acid, wherein the column has a countercurrent stripping section and a rectification section and the recovered acetic acid is introduced into the countercurrent stripping section and/or the rectification section and fresh acetic acid is introduced into the rectification section and the liquid taken off from the column is divided into two substreams and one substream is pumped back into the column with maintenance of a minimum pumped circulation required for sufficient saturation with acetic acid, with this substream being monitored in terms of safety and being heated in a heat exchanger arranged in parallel to at least one further heat exchanger before entering the column, and the other substream is discharged.

2. The method as claimed in claim 1, wherein the heat exchangers are operated alternately.

3. The method as claimed in claim 1, wherein the minimum pumped circulation is at least three times, preferably seven times, the amount of recovered acetic acid introduced.

4. The method of claim 1, wherein the minimum pumped circulation is introduced in the upper part of the countercurrent stripping section.

5. The method as claimed in claim 4, wherein the minimum pumped circulation is introduced at the top of the countercurrent stripping section.

6. The method of claim 1, wherein the minimum pumped circulation is combined with the total amount or part of the recovered acetic acid before it is introduced into the column.

7. The method of claim 1, wherein fresh acetic acid is introduced in the upper part, preferably at the top, of the rectification section.

8. The method of claim 1, wherein the column is configured as a tray column, a packed column or a bubble cap tray column.

9. The method of claim 1, wherein at least one stripping tray, preferably at least two stripping trays, is/are located in the countercurrent stripping section and at least five, preferably at least eight, rectification trays are located in the rectification section.

10. The method of claim 1, wherein the weight ratio of the discharged substream to the substream which is recirculated to the minimum pumped circulation is 1:10–20, preferably 1:13–16.

11. The method of claim 1, wherein acetic acid in the form of fresh acetic acid, recovered acetic acid and minimum pumped circulation is fed in an amount per unit weight of the ethylene-containing gas introduced such that the ethylene-containing gas mixture discharged from the column has an acetic acid content of from 10 to 30% by weight at its saturation point.

* * * * *